(12) United States Patent
Wildschuetz et al.

(10) Patent No.: US 8,604,455 B2
(45) Date of Patent: Dec. 10, 2013

(54) SENSOR ARRANGEMENT

(75) Inventors: Marcus Wildschuetz, Neuss (DE); Matthias Aden, Rimbach (DE)

(73) Assignee: FAUDI Aviation GmbH, Stadtallendorf (DE)

( * ) Notice: Subject to any disclaimer, the term of this patent is extended or adjusted under 35 U.S.C. 154(b) by 128 days.

(21) Appl. No.: 13/128,419

(22) PCT Filed: Nov. 10, 2009

(86) PCT No.: PCT/DE2009/001584
§ 371 (c)(1),
(2), (4) Date: Jun. 30, 2011

(87) PCT Pub. No.: WO2010/051806
PCT Pub. Date: May 14, 2010

(65) Prior Publication Data
US 2011/0249257 A1    Oct. 13, 2011

(30) Foreign Application Priority Data
Nov. 10, 2008  (DE) .......................... 10 2008 056 559

(51) Int. Cl.
*G02B 6/42*  (2006.01)

(52) U.S. Cl.
USPC ................ 250/573; 250/227.11; 250/227.25; 250/227.28; 385/12; 385/129; 356/436

(58) Field of Classification Search
USPC .......... 250/573–577, 227.11, 227.14, 227.23, 250/227.25, 227.28, 227.29; 356/73, 301, 356/436, 440, 441; 385/9, 12, 73, 75, 92, 385/129
See application file for complete search history.

(56) References Cited

U.S. PATENT DOCUMENTS

| | | | |
|---|---|---|---|
| 3,906,241 A | | 9/1975 | Thompson |
| 4,753,530 A | * | 6/1988 | Knight et al. ................... 356/73 |
| 5,678,751 A | | 10/1997 | Buchanan et al. |
| 2007/0103690 A1 | | 5/2007 | Ebersole et al. |

FOREIGN PATENT DOCUMENTS

| | | |
|---|---|---|
| CH | 01635-05 | 10/2005 |
| EP | 0 423 367 | 4/1991 |
| GB | 1460623 | 1/1977 |
| GB | 1554309 | 10/1979 |

\* cited by examiner

*Primary Examiner* — Kevin Pyo
(74) *Attorney, Agent, or Firm* — Clark & Brody

(57) ABSTRACT

The invention relates to an optical sensor array detecting a first liquid medium in a second liquid medium by means of the reflection of an emitted light beam of a given wavelength, comprising a light source and an associated receiver, further two circular glass rod lenses running parallel to each other while encapsulated in a housing. The index of refraction of the glass rod lenses is different from those of the liquid media. A reflecting surface is situated opposite the glass rod lenses and is connected to the housing. Said array also comprises a control fitted with a beam splitter, a second receiver and a third receiver, the latter two receivers being configured being mutually opposite.

13 Claims, 4 Drawing Sheets

SENSOR ARRANGEMENT

FIELD OF THE INVENTION

The present invention relates to an optical sensor arrangement, hereafter sensor array that serves to detect a first liquid medium in a second liquid medium by means of the reflection of an emitted light beam of one wavelength using only one light source and an associated receiver.

BACKGROUND ART

As regards producing, storing and transporting/shipping liquid hydrocarbon-based fuels such as kerosene, it is known that they shall be contaminated with water due not only to contact with humid/moist air but also with storage containers and transporting conduits. Kerosene is hygroscopic and as a result attracts water. Once the solubility limit has been exceeded, first very fine water droplets form as an emulsion in the fuel base. Due to this hygroscopicity, the fine water droplets become larger and thereupon may settle at the bottom in the form of a closed sump phase. Accordingly both free and bound water is frequently present in fuels. Safety requires removing this water periodically to preclude damage in fuel-driven engines. Illustratively the suspended water may be separated by using coalescence separators.

Recently certain fuel additives have become problematic because hampering separating the water from the fuel. Occasionally human failure entails accidentally filling tank facilities with mixtures of fuel and water, or even with water only. In particular in the airline industry, especially high safety requirements must be met. Accordingly it is highly desirable to monitor the entire fuel supply chain from the refinery to tank filling and to rapidly detect both the content of free water and the presence of water instead of fuel and thereby to issue timely warnings and eliminate such dangers.

There are a number of solutions in the state of the art to the above cited difficulties. Both British patents 1,460,623 and 1,554,309 resort to means requiring a measuring chamber. Such designs incur the drawback that in the case of continuous measurements (British patent 1,460,623) only qualitative results are available, or, in the case of discontinuous measurements (British patent 1,554,309), they will result only in quantitative values. These designs do not disclose a detector able to continuously and quantitatively measure free water in fuel and simultaneously the presence of pure water in containers and conduits.

The Swiss patent disclosure 01635-05 discloses another applicable solution. The unit described therein relates to a probe to simultaneously measure light scattering and light absorption at a given wavelength, a first housing being fitted with windows to pass transmitted light respectively scattered light. This Swiss design further comprises a second housing which is closed at one end and is fitted with a recess receiving optical elements to guide and collimate light and having one window transparent to optical radiation. The housing windows are mutually opposite, the housings being linked to each other by a spacer element.

SUMMARY OF THE INVENTION

Such a design however incurs the drawback that the required lenses cannot be adequately sealed against kerosene within both housings. In extended continuous operation, frequently the lens seals against the housings will fail, as a result of which the sensor array ultimately is destroyed. Also self-checking is not feasible in this Swiss design.

Accordingly the objective of the present invention is to discover a sensor array with which to determine continuously, quantitatively suspended free water in fuels as well as the presence of pure water in containers. Such an array also must allow easy maintenance, be durable, and operate reliably. Additionally such an array should be economical to manufacture.

An optical sensor array to detect a first liquid medium in a second liquid medium by means of reflection of a given wavelength and comprising a light source as well as an associated receiver is fitted with two mutually parallel glass rod lenses. The design of the sensor array of the present invention of two glass rod lenses offers a number of advantages. Compared to the use of optic glass fibers and conventional lenses, using the glass rod lenses offers the advantage that the path of the light beam can be predicted and hence be calculated. The optical glass fibers used in the state of the art are bundled and manufactured manually. As a result, previous to the present invention, each optical sensor array differed as regards the beam's path and its index of refraction. Heretofore the electronics at the end of the sensor array always required calibrating the particular bundle of optical glass fibers. Mass production of such sensor arrays was inherently precluded. On the other hand, by using glass rod lenses and consequently eliminating bundled optical glass fibers and conventional lenses, the invention creates an approximately collimated light beam whereby the intensity of the light entering the liquid media is strikingly improved (by a factor of 10 to 100).

This feature considerably reduces the deviations in sensor accuracies, as a result of which a subsequently connected electronics allows more numerous and more accurate readout values. Moreover the connected electronics need not be adjusted to each sensor unit, instead it can be programmed directly together with the calculated beam path. Again the design of the present invention offers large advantages regarding the durability of the sensor array. Previous to the present invention, kerosene frequently penetrated between the conventional lenses and the optical glass fiber bundles because the bonded lenses were unable to withstand changes in pressure as high as 16 bars. The optic beam path was destroyed thereby. By using glass rods as glass rod lenses, the electronics is better protected against kerosene, said glass rods being sealed along their full length with respect to their support.

In an especially advantageous design of the present invention the index of refraction of the glass rods is different from those of the liquid media. The glass rods' refractive index is therefore uniform, this feature being feasible by using special glass. At the transition from glass to liquid, the incident light will be refracted commensurately, i.e. differently with the different indices of refraction and be deflected at a defined angle to the optic axis of the glass rod lenses. Both glass rods are polished angularly because otherwise the desired angle of scattering of 20° would not be attained in spite of using a special glass. The polished faces are designed to be oblique boundary surfaces in a manner that, with respect to kerosene, the beam leaving the glass rods shall be incident on a reflecting surface. The beam is reflected from said reflecting surface back into the same glass rod lens. The indices of refraction of glass and kerosene being different, the light is bent more strongly and does not impinge said reflecting surface. Backward reflection no longer takes place. Compared with the state of the art, this design offers the further advantage of needing only one light source of defined wavelength, the absorption proportion required for water detection no longer needing being determined.

Preferably the glass rod lenses are circular. In this manner they may be rotated within a support about their own optic axis, allowing thereby subsequently adjusting the path of reflection. A sensor array of which the glass rod lenses are encapsulated into a housing furthermore offers the advantage that both the light source and it's associated receiver can be sealed from the portion bathed by the kerosene. In an especially advantageous embodiment mode the glass rod lenses may be made together with the housing. In that embodiment mode the sealing between the housing and the glass rod lenses will be especially durable. Besides being made of a stainless steel, the housing also may be an injection molded unit made of a plastic. As regards a basic injection molded unit, the glass rod lenses may be cast/injected simultaneously with said unit. Besides the already cited advantages, the latter sealing feature also allows economic and compact manufacture.

One sensor array of the present invention, wherein the reflecting surface is situated opposite the glass rod lenses, furthermore offers the advantage of subtending a compact unit. Illustratively, when doing maintenance on the sensor array and when removing/dismantling the housing receiving the glass rod lenses, the reflecting surface can be serviced during the same procedure. This feature is especially advantageous because suspended materials may settle on said reflecting surface and reduce their reflectance. An additional mirror also may be mounted at said reflecting surface for intensification. Said mirror also can be cleaned.

A lens mounted in front of the light source collimates the emitted light and assures balanced light distribution within the glass rod lens. An optical stop situated in front of the receiver constrains the reflection beam impinging the receiver to a given value of light intensity. Moreover a further lens may be configured between the glass rod element to focus the beam onto the receiver.

A control of the transceiver is used in an especially advantageous embodiment mode of the present invention. This design allows checking the operability of the sensor array. Also, it allows determining the degree of soiling of the reflecting surface. Again, said control allows detecting a water hammer without need for absorption measurements. Preferably said control includes a beam splitter and a second receiver. The beam splitter taps a slight proportion of the light flux from the source and reflects it onto the second receiver. This feature allows checking whether the light source is at all operative and how much light it emits.

Preferably also a third receiver is used at the sensor array and is situated opposite the second receiver. The light beam reflected from the reflecting surface impinges the beam splitter which in turn taps a small part of said light's flux and transmits it to the third receiver which in this manner determines the incident light intensity. The ratio of emitted quantity of light to incident quantity of light allows a number of determinations. Among these are: degree of mirror soiling, degree of soiling of the boundary surfaces, presence of a mirror, and possibly the degree of the absorption proportion by water in the kerosene phase. Mounting the two receivers opposite each other allows overall compactness.

BRIEF DESCRIPTION OF THE DRAWINGS

Further features, particulars and advantages of the present invention are defined in the claims and discussed in the description below of illustrative embodiment modes in relation to the appended drawings.

DETAILED DESCRIPTION OF THE INVENTION

Figure 1:
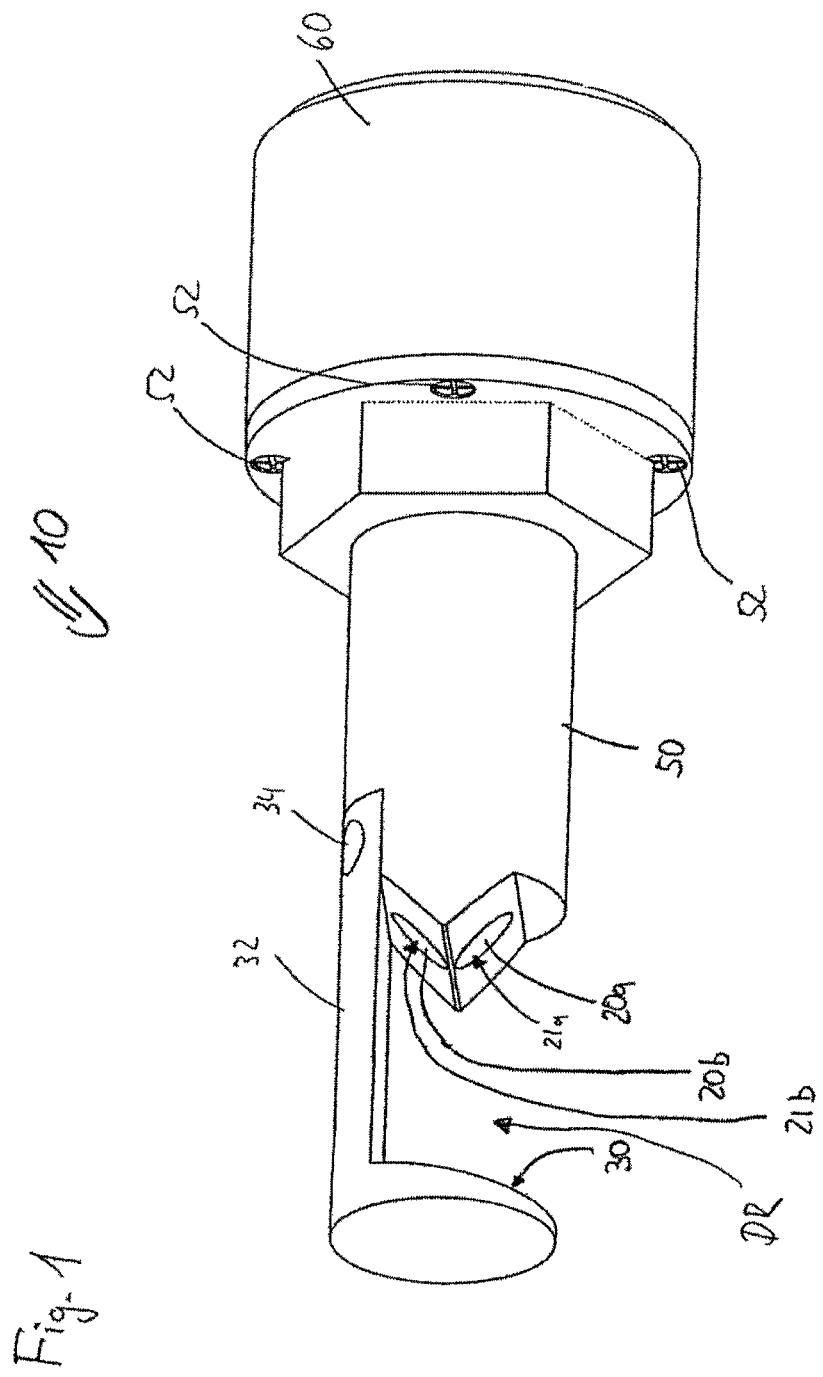
FIG. 1 shows a sensor array of the invention.

FIG. 1 shows a sensor array 10 in its final assembled state before being introduced into a tank or a pipeline. A first and second glass rod lens 20a resp. 20b are shown being entirely encapsulated into a housing 50. This housing 50 matches the boundary surfaces 21a, 21b of the glass rod lenses. Together with a reflecting surface 30 affixed to it, a cantilever 32 is connected by fasteners 34 such as screws to the housing 50. The housing 50 is detachably linked by securing elements 52 with a housing 60 containing the electronics. Both the light source 5 and the receiver 6 are supported in the electronics housing 60. This layout allows easy disassembly of all essential components of the invention and to individually servicing them. A detection space DR is subtended between the reflecting surface 30 and the housing 50. The volume of the detection space DR is known and the water concentration in it is determined. Using correlation, it is possible to approximately extrapolate the data relating to the water concentration in the kerosene to that in the tank or the pipeline. The sensor array may be made especially compact by that feature.

Figure 2:
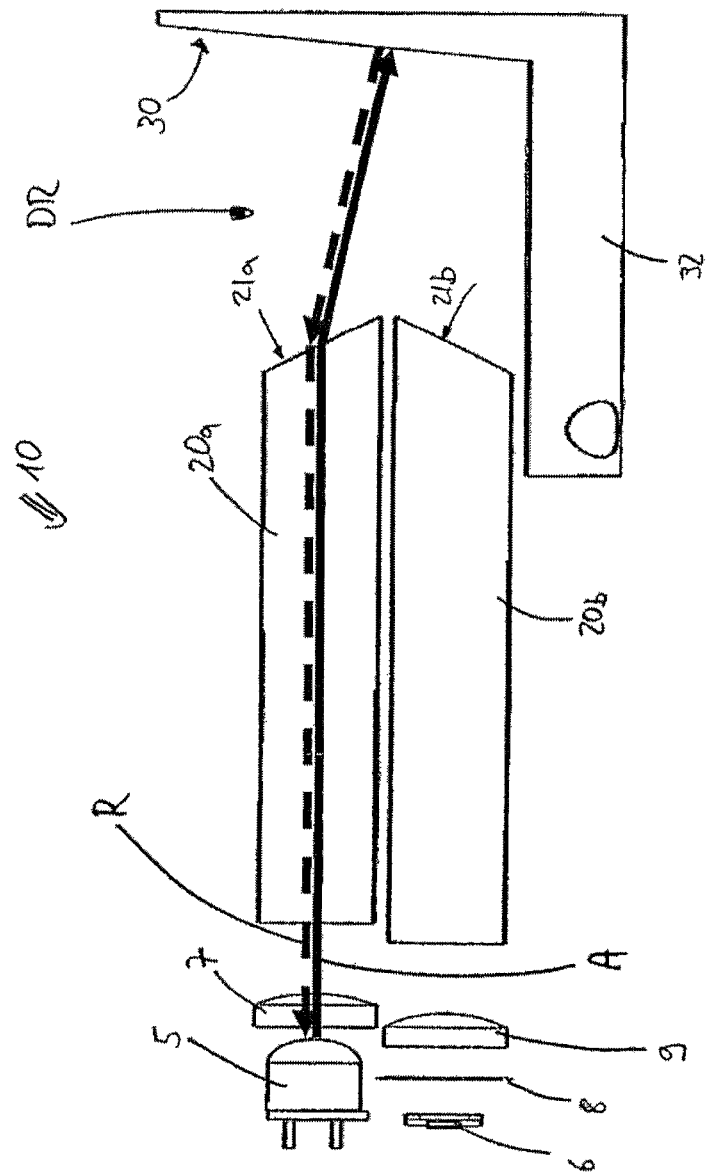
FIG. 2 shows the path taken by the beam when detecting pure kerosene.

FIG. 2 shows the operational principle of the sensor array 10 of the invention when detecting pure kerosene. A light source 5 emits a beam A which is collimated by a conventional lens 7 and in this form is fed into the first glass rod lens 20a. In the process, the glass rod lens 20a directs the light beam A. The light beam A is refracted at the boundary surface 21a where it exits the glass rod lens 20a and then impinges an opposite reflecting surface 30. Specular coatings (mirrors) may be deposited on said reflecting surface 30. The light beam R reflected at the reflection surface 30 is directed back into first glass rod lens 20a. An additional (omitted) receiver may be located at the end of said glass rod lens 20a. The wavelength of the transmitted light is selected in a manner that, for the case of pure kerosene in the detection space DR, the scattered light shall be nearly absorbed. In that case the second glass rod lens 20b will guide little if any emitted light through the lens 9 and the stop 8 toward the scattered light receiver 6.

If there is pure water in the detection space DR, the light beam A is deflected so much that it is no longer reflected back onto the glass rod lens 20a. On the other hand the proportion of stray light would be higher because of the lack of absorption otherwise due to the missing kerosene. Still, the proportion of stray light would pass through the second glass rod lens 20b.

Figure 3:
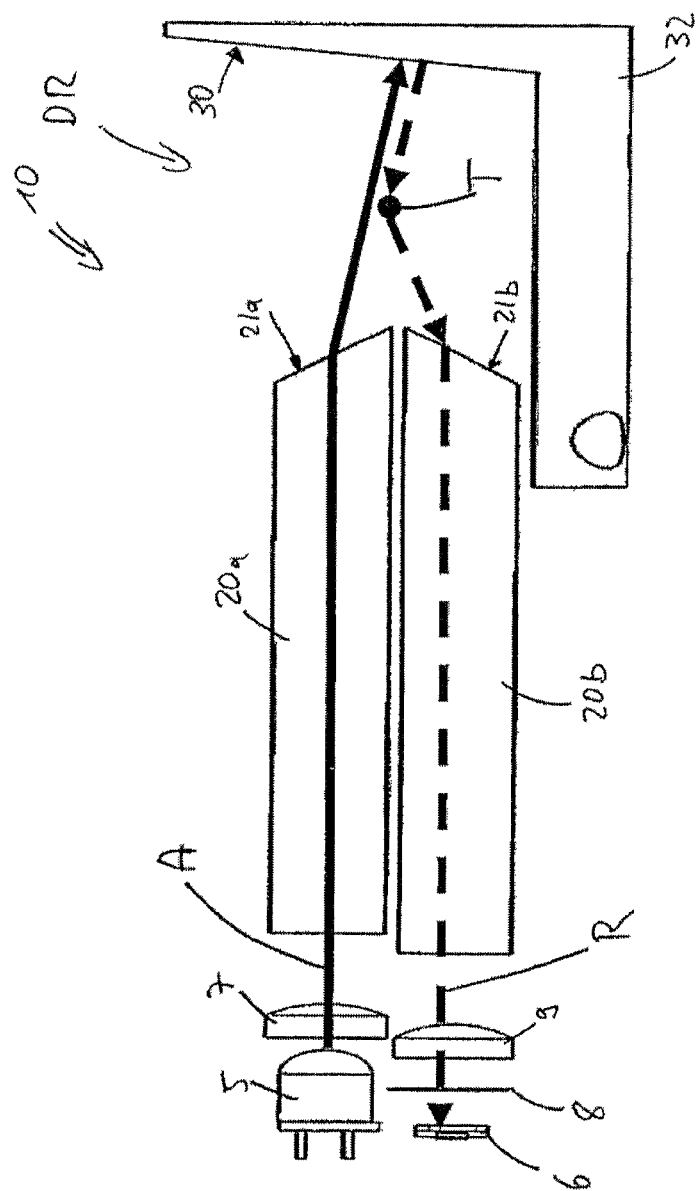
FIG. 3 shows the path taken by the beam when detecting a kerosene/water emulsion.

FIG. 3 shows the operational principle of the sensor array 10 of the invention in the presence of water droplets T. In such a case there will be scattered light which can be detected as being forward and backward scattering. Both effects are used in an embodiment mode of the invention fitted with a reflecting surface 30. The shown forward scattering is especially significant. The emitted light beam A is reflected at the reflecting surface 30 and then hits the water droplets T. The scattered light is made to pass by means of the second glass rod lens 20b through the lens 9 and the optical stop 8 to impinge the receiver 6 which detects it. The sensitivity of the receiver 6 is designed to detect even very low water concentrations (down to 5 ppm water in kerosene). The higher the concentration of water, the more scattered light will enter the second glass rod lens 20b.

Figure 4:
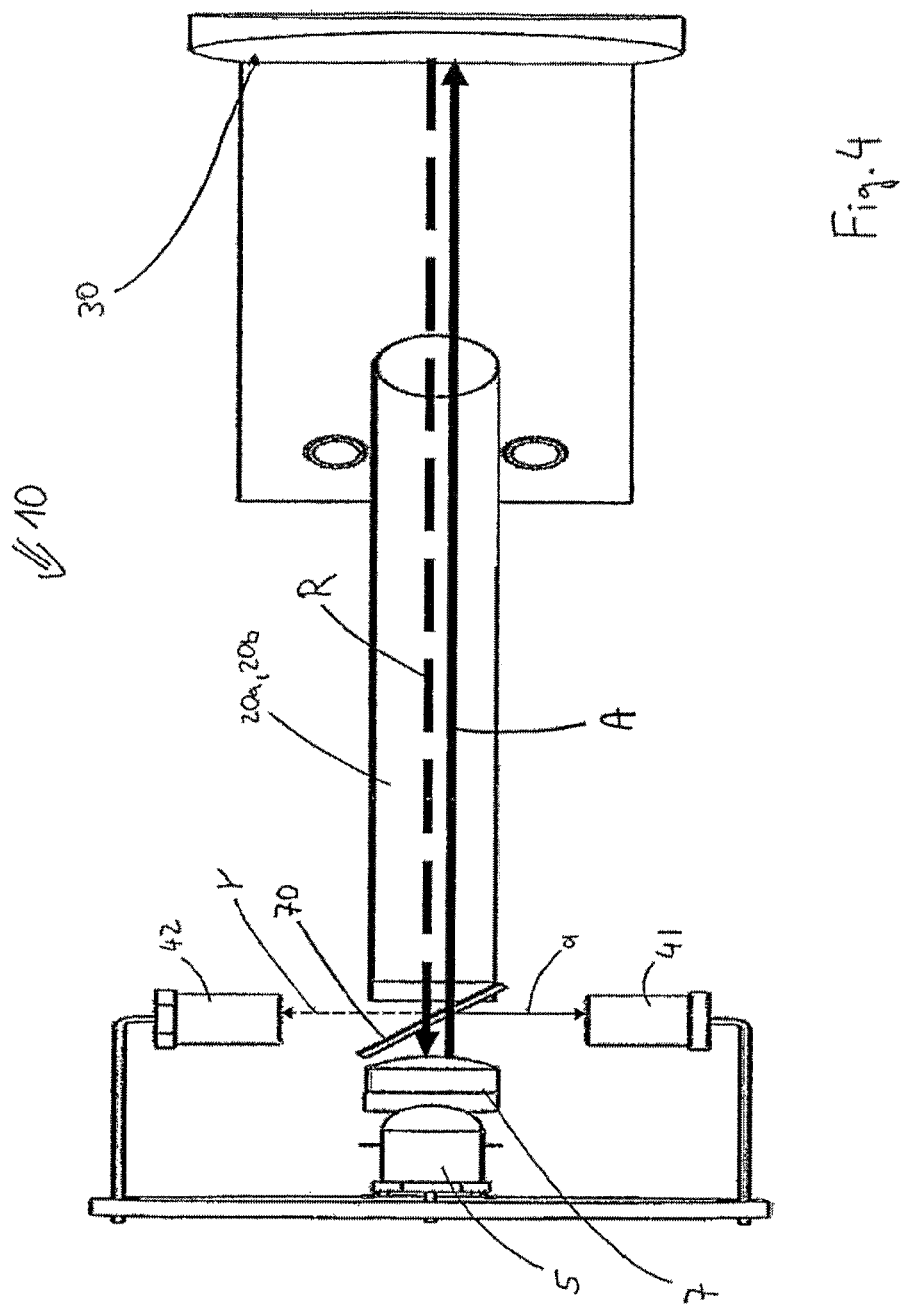
FIG. 4 is the beam path when detecting pure kerosene in a control-fitted sensor array of the invention.

FIG. 4 shows the beam path of an especially advantageous sensor array 10 of the invention wherein the said array is fitted with a control. The sensor array 10 of this embodiment mode has been rotated by 90° relative to FIG. 2. The light beam A exits the light source 5 through the lens 7 and then impinges a beam splitter 70. The light beam A passes through the beam splitter 70 which transmits part of this light to a second receiver 41. This second receiver 41 is a reference cell, preferably a photocell. In this manner the output of the light source 5, hence also the light beam entering the first glass rod lens 20a, can be measured. The light not split from the beam splitter 70 toward the second receiver 41 passes through the first glass rod lens 20a and is refracted when transiting the boundary surface 21a. In the presence of kerosene the light beam A reaches the said reflecting surface where it is reflected and then passes through the first glass rod lens 20a back to the beam splitter 70. The beam splitter 70 diverts a proportion r of the reflected beam R toward a third receiver 42. Measuring the said proportion r allows determining the degrees of soiling of the reflecting surface 30 and of the boundary surface 21a. Preferably the beam proportions (r, a) diverted by the beam splitter 70 are equal as regards the light beams (R, A).

The present invention is not restricted to the above described embodiment modes, but may be modified in versatile manner.

All features and advantages explicit and implicit in and from the claims, specification and drawings, inclusive design details, spatial configurations and procedural steps, may be construed inventive per se as well as in arbitrary combinations.

| List of reference symbols. | |
| --- | --- |
| 5 | light source |
| 6 | receiver |
| 7 | conventional lens |
| 8 | optical stop |
| 9 | conventional lens |
| 10 | sensor array |
| 20 | glass rod lenses |
| 20a | first glass rod lens |
| 20b | second glass rod lens |
| 21a | first boundary surface |
| 21b | second boundary surface |
| 30 | reflecting surface |
| 32 | cantilever |
| 34 | fastener |
| 41 | second receiver |
| 42 | Third receiver |
| 50 | housing |
| 52 | securing element |
| 60 | electronics housing |
| 70 | beam splitter |
| A | light beam |
| R | reflected beam |

| List of reference symbols. | |
| --- | --- |
| DR | detection space |
| T | water droplet |
| a | diverted beam proportion |
| r | diverted beam proportion |

The invention claimed is:

1. An optical sensor array (10) detecting a first liquid medium in a second liquid medium by reflecting an emitted light beam at a given wavelength at a reflecting surface (30), comprising a light source (5) and an associated first receiver (6), comprising:
    two glass rod lenses (20) being configured parallel to each other
    the first glass rod lens (20a) having a polished angular boundary surface (21a) with respect to an optical axis thereof;
    the reflecting surface (30A) being situated opposite the glass rod lenses (20a, 20b);
    the light source being allocated to the first glass rod lens (20a);
    the first receiver being allocated to the second glass rod lens (20b); and
    wherein a light beam leaving the first glass rod lens (20a) through the boundary surface (21a) is affected by light refraction.

2. Sensor array (10) as claimed in claim 1, characterized in that the optical index of refraction of the glass rod lenses (20) differs from those of the liquid media.

3. Sensor array (10) as claimed in claim 1, characterized in that the glass rod lenses (20) are circular.

4. Sensor array (10) as claimed in claim 1, characterized in that the glass rod lenses are encapsulated in a housing (50).

5. Sensor array (10) as claimed in claim 4, characterized in that the reflecting surface (30) is connected to the housing (50).

6. Sensor array (10) as claimed in claim 1, characterized in that a lens (7) is situated in front of the light source (5).

7. Sensor array (10) as claimed in claim 1, characterized in that an optical stop (8) is situated in front of the first receiver (6).

8. Sensor array (10) as claimed in claim 7, characterized in that a further lens (9) is situated in front of the stop (8).

9. Sensor array (10) as claimed in claim 1, characterized in that it includes a control for checking operability of the sensor array.

10. Sensor array (10) as claimed in claim 9, characterized in that the control comprises a beam splitter (70) and a second receiver (41).

11. Sensor array (10) as claimed in claim 10, characterized in that the control comprises a third receiver (42).

12. Sensor array (10) as claimed in claim 11, characterized in that the second receiver (41) and the third receiver (42) are configured mutually opposite.

13. Sensor array (10) as claimed in claim 1, wherein, when only a second medium is detected, the emitted light beam is reflected back into the first glass rod lens (20a).

\* \* \* \* \*